US012788738B2

(12) United States Patent
Della Valle et al.

(10) Patent No.: US 12,788,738 B2
(45) Date of Patent: Nov. 10, 2026

(54) N-PALMITOYLETHANOLAMIDE AND DOCOSAHEXAENOIC ACID FOR USE IN THE TREATMENT OF AUTISM SPECTRUM DISORDER AND OTHER DEPRESSIVE SYNDROMES

(71) Applicant: EPITECH GROUP S.P.A., Milan (IT)

(72) Inventors: Francesco Della Valle, Milan (IT); Maria Federica Della Valle, Milan (IT); Chiara Gomiero, Milan (IT); Gabriele Marcolongo, Milan (IT); Antonio Calignano, Milan (IT); Claudia Cristiano, Milan (IT)

(73) Assignee: EPITECH GROUP S.P.A., Milan (IT)

( * ) Notice: Subject to any disclaimer, the term of this patent is extended or adjusted under 35 U.S.C. 154(b) by 0 days.

(21) Appl. No.: 17/949,754

(22) Filed: Sep. 21, 2022

(65) Prior Publication Data

US 2023/0104124 A1 Apr. 6, 2023

(30) Foreign Application Priority Data

Sep. 23, 2021 (IT) ........................ 102021000024464

(51) Int. Cl.

| | |
|---|---|
| ***A61K 31/202*** | (2006.01) |
| ***A23L 33/00*** | (2016.01) |
| ***A23L 33/12*** | (2016.01) |
| ***A61K 9/00*** | (2006.01) |
| ***A61K 9/48*** | (2006.01) |
| ***A61K 31/16*** | (2006.01) |
| ***A61K 47/02*** | (2006.01) |
| ***A61K 47/12*** | (2006.01) |
| ***A61K 47/22*** | (2006.01) |
| ***A61K 47/26*** | (2006.01) |
| ***A61K 47/36*** | (2006.01) |
| ***A61K 47/38*** | (2006.01) |
| ***A61P 25/00*** | (2006.01) |
| ***A61P 25/24*** | (2006.01) |

(52) U.S. Cl.

CPC ............ *A61K 31/202* (2013.01); *A23L 33/12* (2016.08); *A23L 33/40* (2016.08); *A61K 9/0095* (2013.01); *A61K 9/4825* (2013.01); *A61K 9/4858* (2013.01); *A61K 9/4875* (2013.01); *A61K 31/16* (2013.01); *A61K 47/02* (2013.01); *A61K 47/12* (2013.01); *A61K 47/22* (2013.01); *A61K 47/26* (2013.01); *A61K 47/36* (2013.01); *A61K 47/38* (2013.01); *A61P 25/00* (2018.01); *A61P 25/24* (2018.01); *A23V 2002/00* (2013.01)

(58) Field of Classification Search

CPC .. A61K 31/202; A61K 9/0095; A61K 9/4825; A61K 9/4858; A61K 9/4875; A61K 31/16; A61K 47/02; A61K 47/12; A61K 47/22; A61K 47/26; A61K 47/36; A61K 47/38; A61K 9/08; A61K 9/1623; A61K 31/164; A23L 33/12; A23L 33/40; A61P 25/00; A61P 25/24; A23V 2002/00

See application file for complete search history.

(56) References Cited

U.S. PATENT DOCUMENTS 8,663,701 B2 * 3/2014 Della Valle ............. A61P 15/00 424/489
2011/0237669 A1 9/2011 Stein et al.

FOREIGN PATENT DOCUMENTS

| | | | | |
|---|---|---|---|---|
| EP | 1207870 B1 * | 3/2005 | ............. A61K 31/16 |
| JP | 2016501876 A | 1/2016 | |
| JP | 2017523230 A | 8/2017 | |
| WO | 2016/020828 A1 | 2/2016 | |

OTHER PUBLICATIONS

Bertolino et al., Beneficial Effects of Co-Ultramicronized Palmitoylethanolamide/Luteolin in a Mouse Model of Autism and in a Case Report of Autism. CNS Neurosci Ther. Jan. 2017;23(1):87-98. doi: 10.1111/cns.12648. Epub Oct. 4, 2016. PM (Year: 2017).*

Pangrazzi L, Balasco L, Bozzi Y. Natural Antioxidants: A Novel Therapeutic Approach to Autism Spectrum Disorders? Antioxidants (Basel). Nov. 26, 2020;9(12):1186. doi: 10.3390/antiox9121186. PMID: 33256243; PMCID: PMC7761361. (Year: 2020).*

Peritore AF, Siracusa R, Crupi R, Cuzzocrea S. Therapeutic Efficacy of Palmitoylethanolamide and Its New Formulations in Synergy with Different Antioxidant Molecules Present in Diets. Nutrients. Sep. 11, 2019;11(9):2175. doi: 10.3390/nu11092175. PMID: 31514292; PMCID: PMC6769461. (Year: 2019).*

Antonucci N, Cirillo A, Siniscalco D. Beneficial effects of palmitoylethanolamide on expressive language, cognition, and behaviors in autism: A report of two cases. Case Rep Psychiatry 2015;2015:325061. (Year: 2015).*

Product Information: Glialia® 700 mg+70 mg Microgranules (https://shop.epitech.it/en/product/glialia-700-mg-70-mg-microgranules/) (Year: 2024).*

Petrosino et al. "The pharmacology of palmitoylethanolamine and first data on the therapeutic efficacy of some of its new formulations" (2016); Br J Pharmacol Sep. 29; 174(11):1349-1365. (Year: 2016).*

Search Report for Italian Patent Application No. 102021000024464 dated Apr. 25, 2022, 9 pages.

Chew, L. et al., "Association of Serum Allopregnanolone with Restricted and Repetitive Behaviours in Adult Males with Autism", Psychoneuroendocrinology, 123: 1-21 (Jan. 2021).

Crawley, J., "Designing Mouse Behavioral Tasks Relevant to Autistic-Like Behaviors", Mental Retardation and Developmental Disabilities Research Reviews, 10: 248-258 (2004).

(Continued)

*Primary Examiner* — James H Alstrum-Acevedo
*Assistant Examiner* — Chantal Adlam
(74) *Attorney, Agent, or Firm* — Merchant & Gould P.C.

(57) ABSTRACT

N-palmitoylethanolamide (PEA) is used in combination with docosahexaenoic acid (DHA) in the treatment of autism spectrum disorder and other depressive syndromes. In particular, N-palmitoylethanolamide (PEA) is used in combination with docosahexaenoic acid (DHA) in the treatment of diseases having decreased endogenous levels of allopregnanolone.

17 Claims, 2 Drawing Sheets

(56) References Cited

OTHER PUBLICATIONS

Ebihara, K. et al., "Decrease in endogenous brain allopregnanolone induces autism spectrum disorder (ASD)-like behavior in mice: A novel animal model of ASD", Behavioural Brain Research 334: 6-15 (2017).
McFarlane, H.G. et al., "Autism-like behavioral phenotypes in BTBR T+tf/J mice", Genes, Brain and Behavior, 7: 152-163 (2008).
Paylor, R., et al., "The use of behavioral test batteries, II: Effect of test interval", Physiology & Behavior, 87: 95-102 (2006).
Peritore, A.F. et al., "Therapeutic Efficacy of Palmitoylethanolamide and Its New Formulations in Synergy with Different Antioxidant Molecules Present in Diets", Nutrients, 11(9): 1-22 (2019).
Russo, R. et al., "Gut-brain Axis: Role of Lipids in the Regulation of Inflammation, Pain and CNS Diseases", Current Medicinal Chemistry, 24: 1-22 (2014).
Remington, The Science and Practice of Pharmacy, ed by Allen, Loyd V., Jr., 22nd edition, chapter 38, 39 and 45 (2012).
Scattoni, M. L. et al., "Unusual Repertoire of Vocalizations in the BTBR T+tf/J Mouse Model of Autism", PLos One, 3(8): 1-15 (Aug. 2008).
Wahlsten, D. et al., "Survery of 21 inbred mouse strains in two laboratories reveals that BTBR T/+ tf/tf has severly reduced hippocampal commissure and absent corpus callosum", Brain Research, 971: 47-54 (2003).
Zou, M. et al., "Role of the endocannabinoid system in neurological disorders", International Journal of Developmental Neurosciences, 76: 95-102 (2019).
"2.9.31: Particle Size Analysis by Laser Light Diffraction," European Pharmacopoeia 8.0.
Barbierato et al., "Co-ultramicronized Palmitoylethanolamide/ Luteolin Promotes the Maturation of Oligodendrocyte Precursor Cells," Scientific Reports 5:16676 (Nov. 18, 2015).
Bozzatello et al., "Supplementation with Omega-3 Fatty Acids in Psychiatric Disorders: A Review of Literature Data," Journal of Clinical Medicine 5(67): 26 pages (2016).
Bent, Stephen et al., Original Paper "A Pilot randomized Controlled Trial of Omega-3 Fatty Acids for Autism Spectrum Disorder," J Autism Dev Disord (2011) 41:545-554; DOI 10.1007/s10803-010-1078-8.
De la Torre-Aguilar, Maria Jose et al., Docosahexaenoic and Eicosapentaenoic Intervention Modified Plasma and Erythrocyte Omega-3 Fatty Acid Profiles But Not the Clinical Course of Children With Autism Spectrum Disorder: A Randomized Control Trial, Frontiers in Nutrition, clinical trial published: Mar. 29, 2022, vol. 9; Article 790250; pp. 1-14.
Parellada, Mara, et al., "Randomized trial of omega-3 for autism spectrum disorders: Effect on cell membrane composition and behavior," European Neuropsychopharmacology (2017), http://dx.doi.org/10.1016/j.euroneuro.2017.08.426, pp. 1-12.
Van Elst, Kim et al., "Food for thought: Dietary changes in essential fatty acid ratios and the increase in autism spectrum disorders," Neuroscience and Biobehavioral Reviews 45 (2014) pp. 369-378.
Mankad, Deepali, et al., "A randomized, placebo controlled trial of omega-3 fatty acids in the treatment of young children with autism," Mankad et al. Molecular Autism (2015) 6:18 DOI 10.1186/s13229-015-0010-7, pp. 1-11.
Amminger, G. Paul et al., "Omega-3 Fatty Acids Supplementation in Children with Autism: A Double-blind Randomized, Placebo-controlled Pilot Study," Brief Report, Biol Psychiatry 2007; 61:551-553, www.sobp.org/journal.
Barbierato, Massimo et al., "Co-ultramicronized Palmitoylethanolamide/ Luteolin Promotes the Maturation of Oligodendrocyte Precursor Cells," Scientific Reports, 5:16676; DOI: 10.1038/srep16676, Published: Nov. 18, 2015, www.nature.com/scientificreports.
Bent et al. Omega-3 Fatty Acids for Autistic Spectrum Disorder: A Systematic Review. J Autism Dev Disorders 39:1145-54 (2009) at 1145.
Antonucci et al. Beneficial Effects of Paln1itoylethanolan1ide on Expressive Language, Cognition, and Behaviors in Autism: A Report of Two Cases. Case Reports in Psychiatry (2015) (pp. 1-6).
Pangrazzi et al. Natural Antioxidants: A Novel Therapeutic Approach to Autism Spectrum Disorders? Antioxidants 2020, 9, 1186; doi:10.3390/antiox9121186 at Table 1.
Nimbley et al., 2022. Sensory processing and eating behaviours in autism: A systematic review. Eur Eat Disorders Rev. 2022;30:538-559. DOI: 10.1002/erv.2920.
Doherty et al., 2025. Complementary and Alternative Medicine for Autism—A Systematic Review. Journal of Autism and Developmental Disorders (2025) 55:3689-3699. DOI: 10.1007/s10803-024-06449-5.
Lo Verme et al. The Nuclear Receptor Peroxisome Proliferator-Activated Receptor-α Mediates the Anti-Inflammatory Actions of Palmitoylethanolamide. Mol Pharmacol 67(1):15-9 (2005).
Diep et al. Docosahexaenoic Acid, a Peroxisome Proliferator-Activated Receptor-α Ligand, Induces Apoptosis in Vascular Smooth Muscle Cells by Stimulation of p38 Mitogen-Activated Protein Kinase. Hypertension 36(5):851-5 (2000).
Adami et al. Production of PEA composite microparticles with polyvinylpyrrolidone and luteolin using Supercritical Assisted Atomization. J Supercrit Fluids 143:82-9 (2019).
Paterniti et al. A new co-ultramicronized composite including palmitoylethanolamide and luteolin to prevent neuroinflammation in spinal cord injury. J Neuroinflammation 10:91 (2013).
Bertolino et al. Beneficial Effects of Co~Ultramkronized Palmitoylethanolamide/Luteolin in a Mouse Model of Autism and in a Case Report of Autism. CNS Neuroscience & Therapeutics 23 (2017) 87-98.
Petrosino and Di Marzo. The pharmacology of palmitoylethanolamide and first data on the therapeutic efficacy of some of its new formulations. British Journal of Pharmacology (2017) 174, 1349-1365.
Filogamo et al. Low-dose combination of ultramicronized palmitoylethanolamide and docosahexaenoic acid on neurosteroid and neuroinflammatory dysregulation in autism spectrum disorders. Neurotherapeutics, https://doi.org/10.1016/j.neurot.2025.e00816.
Japanese Office Action received for JP Application No. 2022-151373 on Jun. 23, 2026, 14 pgs.

* cited by examiner

N-PALMITOYLETHANOLAMIDE AND DOCOSAHEXAENOIC ACID FOR USE IN THE TREATMENT OF AUTISM SPECTRUM DISORDER AND OTHER DEPRESSIVE SYNDROMES

CROSS-REFERENCE TO RELATED APPLICATION

This application claims the benefit of Serial No. 102021000024464, filed 23 Sep. 2021 in Italy and which application is incorporated herein by reference. To the extent appropriate, a claim of priority is made to the above disclosed application.

TECHNICAL FIELD OF THE INVENTION

The present invention relates to the use of N-palmitoylethanolamide (PEA) in combination with docosahexaenoic acid (DHA) in the treatment of autism spectrum disorder and other depressive syndromes.

BACKGROUND ART

Autism spectrum disorder (ASD) is a multifactorial-etiology neurodevelopmental disorder which manifests through the impairment of social interaction, verbal and non-verbal communication, activities, and interest (definition from the *American Psychiatric Association*). The symptomatology begins within the first three years of life following a specific event and early diagnosis is very important to be able to adequately intervene on the various compromised areas.

Stereotypes are one of the main diagnostic features of ASD and can comprise self-stimulatory and self-harming behaviors, excitement, stimulation, stress, anxiety, boredom, fatigue, and social isolation.

Although the cause is not known, the appearance of ASD is also due to an imbalance between inhibitory and excitatory synapses, as well as neuroinflammation responsible for the activation and pathological proliferation of non-neuronal cells which, by releasing cytokines (IL-1α, IL-1β, IL-6 and TNF-α) and pro-inflammatory chemokines (MCP-1 and RANTES) in the brain and cerebrospinal fluid of autistic patients, exacerbate the neuroinflammatory process.

It is further known that a class of endogenous hormones, known as neurosteroids, are involved in ASD: the most important is allopregnanolone (ALLO), a potent metabolite of progesterone and modulator of $GABA_A$ receptors synthesized by 5α-reductase type 1 enzymes and 3α-hydroxysteroid dehydrogenase. ALLO possesses antidepressant, anxiolytic, anti-stress, sedative, anti-aggressive and analgesic properties and prevents the formation and release of pro-inflammatory cytokines, such as NFkB, HMGB1, MCP-1 and TNF-α involved in multiple neuroinflammatory conditions.

The reduction in plasma and brain ALLO levels found in patients with ASD is strongly correlated with the severity of autistic symptomatology.

The drugs authorized and administered to patients with ASD are risperidone and methylphenidate, which, although useful for treating autistic symptoms, do not act on the modulation of neuroinflammation and on the increase in endogenous ALLO levels.

A drastic reduction in endogenous ALLO levels has also been found in psychiatric conditions such as major depressive disorder (MDD), post-traumatic stress disorder (PTSD) and especially in postpartum depression.

Only in 2019, ALLO, known as Brexanolone, was placed on the market in the United States under the name of Zulresso™ as an intravenous infusion to be administered over 2.5 days. Zulresso™ is the first drug approved by the FDA (Federal Drug Administration) for its exclusive use in the treatment of postpartum depression. In 2016, the EMA included Brexanolone in a study program prior to its marketing in Europe.

Although it is declared an effective and safe drug, Zulresso™ should only be administered in certified healthcare facilities due to the risk of excessive sedation, sudden loss of consciousness or dizziness during the 60 hours of administration.

To date, there are no clinical studies in which ALLO is administered as a therapy for autistic patients: it is thus of considerable importance to identify an anti-neuroinflammatory treatment which is easy to administer orally, safe and free of significant side effects in the long term and capable of also normalizing endogenous ALLO levels.

A natural mechanism for modulating neuroinflammation is the endogenous molecule Palmitoylethanolamide (PEA). In pre-clinical and clinical settings, the administration of PEA, especially if in an ultra-micronized form (PEA-um), is capable of determining neuroinflammatory normalization activity; in particular, it has been demonstrated that PEA-um is capable of significantly sub-modulating the general neuroinflammatory status of mice with a simil-autistic phenotype, reducing the expression of the pro-inflammatory hippocampal and serum cytokines IL-6, IL-1b and TNF-α and modulating the altered behavioral status. Clinically, the 3-month treatment of autistic children with PEA-um 600 mg/day improves aggressiveness, cognitive and behavioral skills, and communication without adverse effects.

DHA (C22:6 n-3) is one of the most abundant long-chain polyunsaturated fatty acids (PUFAs) in the body. It is a fundamental component of all cell membranes, including the cells of the nervous system. The decrease thereof can trigger a malfunction of nervous tissue, negatively affecting learning and behavioral processes as well as aggravating the autistic disease.

Clinical trials have been conducted in patients with ASD by means of administration of PUFA, typically a mixture of EPA and DHA, at high doses (generally greater than 1 g per day), but the results have been poor and insignificant.

Therefore, there is a need to provide ASD therapy which is effective, non-invasive and safe and which, if possible, does not require the administration of high doses of active substances. In fact, taking into account that such therapy would be primarily dedicated to a child population, repeated administration and/or in large dosage forms (for example, large tablets for oral administration of high doses of active ingredients) would be difficult to accept by the patient.

SUMMARY OF THE INVENTION

The present invention derives from the surprising discovery that palmitoylethanolamide (PEA), preferably when used in an ultra-micronized form, when administered in combination with docosahexaenoic acid (DHA), exhibits a synergistically relevant effect in improving the behavioral parameters of autistic subjects and in raising endogenous allopregnanolone (ALLO) levels.

Therefore, the present invention relates to palmitoylethanolamide for use in the treatment of autism spectrum disorders (ASDs), where palmitoylethanolamide is administered in association with docosahexaenoic acid, where said administration is separate, combined, or simultaneous.

The invention further relates to a composition containing palmitoylethanolamide and docosahexaenoic acid, in particular when usable in the treatment of autism spectrum disorders (ASD).

The invention also relates to palmitoylethanolamide for use in the treatment of diseases characterized by decreased endogenous allopregnanolone levels, where palmitoylethanolamide is administered in combination with docosahexaenoic acid, where said administration is separate, combined, or simultaneous.

These and further objects, as outlined in the appended claims, will be described in the following description. The text of the claims should be considered included in the description in order to assess the description sufficiency.

Further features and advantages of the invention will become apparent from the following description of preferred embodiments, given by way of non-limiting examples.

DETAILED DESCRIPTION OF THE INVENTION

Figure 1:
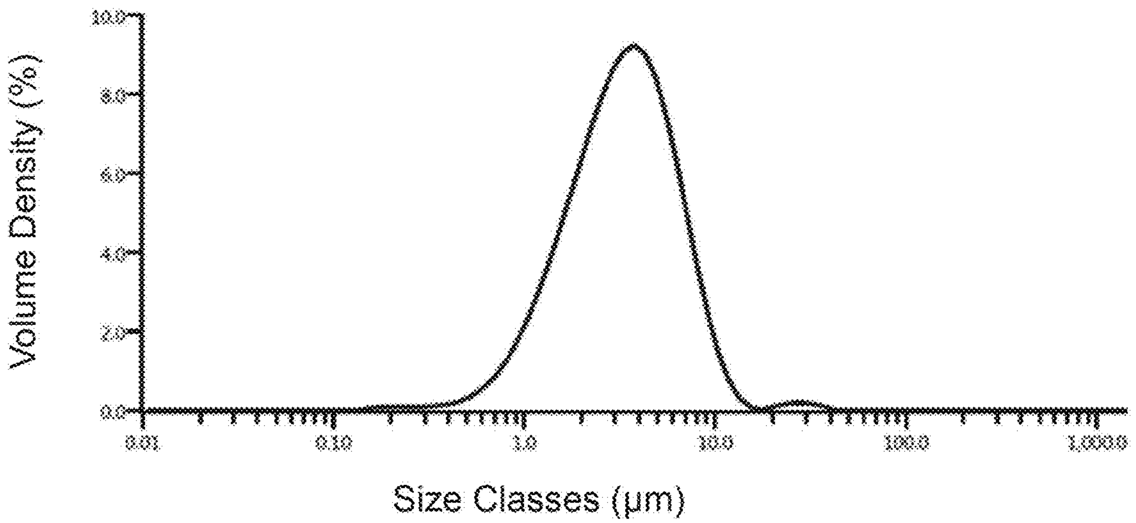
FIG. 1 shows a graph of particle size distribution of palmitoylethanolamide in an ultra-micronized form (PEA-um)

The present invention relates in a first aspect to palmitoylethanolamide (PEA) for use in the treatment of autism spectrum disorders (ASD), where palmitoylethanolamide is administered in association with docosahexaenoic acid (DHA), where said administration is separate, combined, or simultaneous.

The term "in association" means both a combination therapy and a therapy in which PEA and DHA are contained in a single dosage form.

"Separate" administration means an administration of PEA and DHA in separate dosage forms, administered at different times ranging from 1 minute to several hours, for example 8, 12 or 14 hours apart.

"Combined" administration means an administration of PEA and DHA contained in a single dosage form, i.e., a pharmaceutical or veterinary composition or formulation, supplement, dietary composition or food for special medical purposes.

"Simultaneous" administration means an administration of PEA and DHA in separate dosage forms, but administered simultaneously, i.e., within a separation time between the PEA and DHA administration, or vice versa, not exceeding 1 minute.

Palmitoylethanolamide can be administered in any form, for example in a non-micronized form, in a micronized form or in an ultra-micronized form.

The term "palmitoylethanolamide (or PEA) in a non-micronized form" means PEA having a particle size distribution, defined as a percentage by volume and measured with the laser light scattering method, represented by a distribution curve having the mode above 10 microns, preferably above 20 microns.

The term "palmitoylethanolamide (or PEA) in a micronized form" means PEA having a particle size distribution, defined as a percentage by volume and measured with the laser light scattering method, represented by a distribution curve having the mode between 6 microns and 10 microns.

The term "palmitoylethanolamide (or PEA) in an ultra-micronized form" means PEA having a particle size distribution, defined as a percentage by volume and measured with the laser light scattering method, represented by a distribution curve having the mode below 6 microns and above 0.5 microns.

Preferably, the PEA is in an ultra-micronized form.

In an embodiment, the PEA in an ultra-micronized form has a particle size distribution as defined above, measured with a Malvern Mastersizer 3000 instrument with Fraunhofer calculation algorithm, where at least 95% by volume, more preferably at least 99% by volume, of particles has a particle size of less than 6 microns.

In a particularly preferred embodiment, the PEA in an ultra-micronized form has a particle size distribution as defined above, measured with a Malvern Mastersizer 3000 instrument with Fraunhofer calculation algorithm, having a mode between 2 and 4 microns and having 100% by volume of particles smaller than 10 microns and at least 60% by volume of particles smaller than 3 microns.

The micronization can be carried out in a fluid jet system (for example, Jetmill® model system) which operates with spiral technology with a compressed air or nitrogen jet capable of exploiting kinetic energy—instead of mechanical energy—to crush the particles. Such apparatuses are conventional and will therefore not be further described, except in relation to the following features:

Internal diameter of the micronization chamber about 300 mm;

Fluid jet pressure 10-12 bar;

Product supply 9-12 kg/h.

Docosahexaenoic acid (DHA) belongs to the so-called PUFAs or long-chain polyunsaturated fatty acids and has the following structural formula:

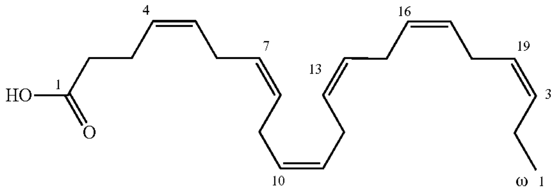

Docosahexaenoic acid (DHA), also called cervonic acid, is an omega-3 or PUFA n-3 fatty acid. Oceanic: cold-water fish are rich in DHA. Most of the DHA present in fish and complex organisms, which live in cold ocean waters, comes from photosynthetic algae. DHA is also commercially produced by microalgae, *Crypthecodinium cohnii* which is a microorganism of the genus *Schizochytrium*. DHA produced using microalgae is of plant origin.

The present invention further relates to a composition comprising palmitoylethanolamide and docosahexaenoic acid. Preferably, the composition of the invention consists of a mixture of palmitoylethanolamide and docosahexaenoic acid and pharmaceutically acceptable excipients. More preferably, palmitoylethanolamide is in an ultra-micronized form (PEA-um).

Whether administered separately or combined in a single formulation, PEA and DHA are administered in a weight ratio between 1:7 and 7:1.

More in particular, when PEA is in an ultra-micronized form, the PEA/DHA weight ratio will preferably be between 1:7 and 1:1, more preferably between 1:5 and 1:2.

When the PEA is in a micronized or non-micronized form, the PEA/DHA weight ratio will preferably be between 1:1 and 7:1, more preferably between 2:1 and 5:1.

For the purposes of the invention, PEA alone, DHA alone or the composition containing PEA and DHA can be included in pharmaceutical or veterinary formulations and can be formulated in dosage forms for oral, buccal, parenteral, rectal or transdermal administration.

For oral administration, the compounds of the invention can be found, for example, in the form of tablets or capsules, hard or soft, prepared in the conventional fashion with pharmaceutically acceptable excipients such as binders (e.g., pregelatinized cornstarch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or inhibiting agents (e.g., sodium lauryl sulfate). The tablets can be coated by methods well known in the art. The liquid preparations for oral administration can be, for example, in the form of solutions, syrups or suspensions or they can be freeze-dried or granulated products to be reconstituted, before use, with water or other suitable vehicles. Such liquid preparations can be prepared through conventional methods with pharmaceutically acceptable additives such as suspending agents (e.g., sorbitol syrup, cellulose derivatives, or edible hydrogenated fats); emulsifiers (e.g., lecithin or acacia); non-aqueous vehicles (e.g., almond oil, oily esters, ethyl alcohol or fractionated vegetable oils); and preservatives (e.g., methyl- or propyl-p-hydroxybenzoates or sorbic acid). The preparation can also conveniently contain flavorings, dyes, and sweeteners.

The preparations for oral administration can be appropriately formulated to allow the controlled release of the active constituent.

For buccal administration, the compounds of the invention can be in the form of tablets or pills formulated in the conventional manner, which are suitable for an absorption at the level of the buccal mucosa. Typical buccal formulations are tablets for sub-lingual administration.

The compounds of the invention can be formulated for parenteral administration by injection. The injection formulations can be presented as a single dose, for example in vials, with an added preservative. The compositions can appear in such a form as suspensions, solutions, or emulsions in oily or aqueous vehicles and can contain agents of the formulation such as suspension, stabilizers and/or dispersants. Alternatively, the active ingredient or the mixture of active ingredients can be found in the form of a powder to be reconstituted, before use, with a suitable vehicle, for example with sterile water.

The compounds of the invention can also be formulated according to rectal formulations such as suppositories or retention enemas, for example containing the basic components of the common suppositories such as cocoa butter or other glycerides.

In addition to the formulations described above, the compounds of the invention can also be formulated as a deposit preparation. Such long-acting formulations can be administered by implantation (e.g., subcutaneously, transcutaneously or intramuscularly) or intramuscular injection. Therefore, for example, the composition can be formulated with appropriate polymer or hydrophobic materials (for example in the form of an emulsion in a suitable oil) or ion exchange resins or as minimally soluble derivatives.

According to the present invention the daily dose of PEA proposed for administration to a man (with body weight of about 70 kg) ranges from 10 mg to 1500 mg or, if PEA is used in an ultra-micronized form, from 10 mg to 500 mg of PEA. Such a daily dose can be divided into dose units for an administration, for example, from 1 to 4 times a day. The dose will depend on the form in which the PEA is administered, i.e., whether non-micronized PEA, micronized PEA or ultra-micronized PEA is administered. The dose will also depend on the route chosen for administration. It should be considered that it may be necessary to continuously vary the dosage depending on the age and weight of the patient and also on the severity of the clinical condition to be treated. The exact dose and route of administration will ultimately be at the discretion of the treating physician or veterinarian.

The invention further relates to dietary compositions, food supplements and foods for special medical purposes (FSMPs) comprising PEA, preferably ultra-micronized PEA, and DHA for use in the treatment of ASD.

The term "food for special medical purposes" means products authorized according to regulation (EU) 2016/128. Such a term refers to a product to be administered under medical supervision, thus assimilating such an FSMP to a drug.

The formulations according to the invention can be prepared according to conventional methods, such as those described in Remington's Pharmaceutical Sciences Handbook, Mack Pub. Co., N.Y., USA, 17th edition, 1985 or in Remington, The Science and Practice of Pharmacy, Edited by Allen, Loyd V., Jr, 22nd edition, 2012.

EXPERIMENTAL SECTION

Micronization Procedure

The PEA was micronized as previously described.

The ultra-micronization was carried out in a fluid jet system (in particular, the Jetmill® model system) which operates with compressed air jet "spiral technology".

Optimal Micronization Conditions:

- internal diameter of the micronization chamber 300 mm;
- fluid jet pressure 8 bar;
- product supply 9-12 kg/h.

Determination of the Particle Size Distribution

The determination of the particle size distribution was carried out on a wet sample, after 1-minute sonication.

A Malvern Mastersizer 3000 instrument operating with the LALLS (Low Angle Laser Light Scattering) technique and a Fraunhofer calculation algorithm was used.

The particle size distribution graph is shown in FIG. 1.

Biological Experimentation

Healthy male C57BL/6J (C57) mice and 90-day BTBR T+tf/J (BTBR) mice (The Jackson Laboratory, Bar Harbor, ME, USA) fed ad libitum and housed in controlled sleep/wake cycle cages were used in the in vivo trial. Before the start of the experimentation, the animals were subjected to an acclimatization period of 1 week considering all the experimental procedures and protocols, compliant with the principles of care and welfare of laboratory animals approved by the Italian Ministry of Health (Italian Legislative Decree 2014/26) and European directives (EU Directive 2010/63).

BTBR mice have a simil-autistic phenotype capable of reproducing the main symptoms of ASD with the appearance of behavioral deficits in a period comparable to early childhood. By virtue of the numerous polymorphisms due to the mutations of individual nucleotides involved in the development of the nervous system and synapses, BTBR mice are completely free of the corpus callosum and subject to severely reduced hippocampal commissure (Wahlsten D. et al., *Survey of* 21 *inbred mouse strains in two laboratories reveals that BTBR T/+tf/tf has severely reduced hippocampal commissure and absent corpus callosum*, Brain Res. 2003, 971: 47-54) This strain has several symptoms of autism including reduced social interactions, altered expressions of play, reduced exploratory behavior, unusual vocalizations, and anxiety (McFarlane H G et al., *Autism-like behavioral phenotypes in BTBR T+tf/J mice*, Genes Brain Behav. 2008, 7: 152-63; Scattoni M L et al., *Unusual repertoire of vocalizations in the BTBR T+tf/J mouse model of autism*, PLoS One 2008, 3: e3067); further has particularly reduced ALLO levels (Ebihara K. et al., *Decrease in endogenous brain allopregnanolone induces autism spectrum disorder (ASD)-like behavior in mice: A novel animal model of ASD*, Behav Brain Res. 2017, 334: 6-15; Chew L. et al., *Association of serum allopregnanolone with restricted and repetitive behaviors in adult males with autism Psychoneuroendocrinology,* 2021, 123: 105039).

Experimental Methods and Results

Healthy C57 animals and BTBR animals were randomized into 8 groups of 8 mice each and treated per os, starting from the fourth month of life, with 1.5% carboxymethyl cellulose (CMC) (vehicle used to suspend molecules), with 1 mg/kg ultra-micronized PEA (PEA-um) alone, with 5 mg/kg DHA alone (30 mg/kg DHA 17% titer) and with 1 mg/kg PEA-um associated with 5 mg/kg DHA (30 mg/kg DHA 17% titer), daily for 10 days:

Group 1: C57 mice treated with 1.5% CMC as control (CTR);

Group 2: C57 mice treated with 1 mg/kg PEA-um suspended in 1.5% CMC (PEA);

Group 3: C57 mice treated with 5 mg/kg DHA (30 mg/kg DHA 17% titer) suspended in 1.5% CMC (DHA);

Group 4: C57 mice treated with 1 mg/kg PEA-um and 5 mg/kg DHA (30 mg/kg DHA 17% titer) suspended in 1.5% CMC (PEA+DHA composition);

Group 5: BTBR mice treated with 1.5% CMC (CTR);

Group 6: BTBR mice treated with 1 mg/kg PEA-um suspended in 1.5% CMC (PEA);

Group 7: BTBR mice treated with 5 mg/kg DHA (30 mg/kg DHA 17% titer) suspended in 1.5% CMC (DHA);

Group 8: BTBR mice treated with 1 mg/kg PEA-um and 5 mg/kg DHA (30 mg/kg DHA 17% titer) suspended in 1.5% CMC (PEA+DHA composition).

The animals were euthanized 10 days after starting the administration of the treatments. Plasma was collected for dosing with the HLPC (Agilent) method of the ALLO neurosteroid. Before being sacrificed, the animals were subjected to behavioral tests to study the repetitive/obsessive phenotype (Marble Burying test and Self Grooming test) and sociability.

All the behavioral tests were conducted by the same mice with a sufficient time interval between one test and the other and starting from the least stressful one (Paylor R. et al., *The use of behavioral test batteries, II: effect of test interval*, Physiol. Behav. 2006, 87: 95-102).

Statistical Analysis

All the values reported in the results are expressed as mean±standard error of the mean (SEM) of N observations (N=number of animals). The statistical differences in the ALLO dosage and behavioral score were analyzed with one-way ANOVA, followed by Sidak's multiple comparisons. P-value <0.05 is considered significant.

Detection of Obsessive and Repetitive Behavior

Figure 2:
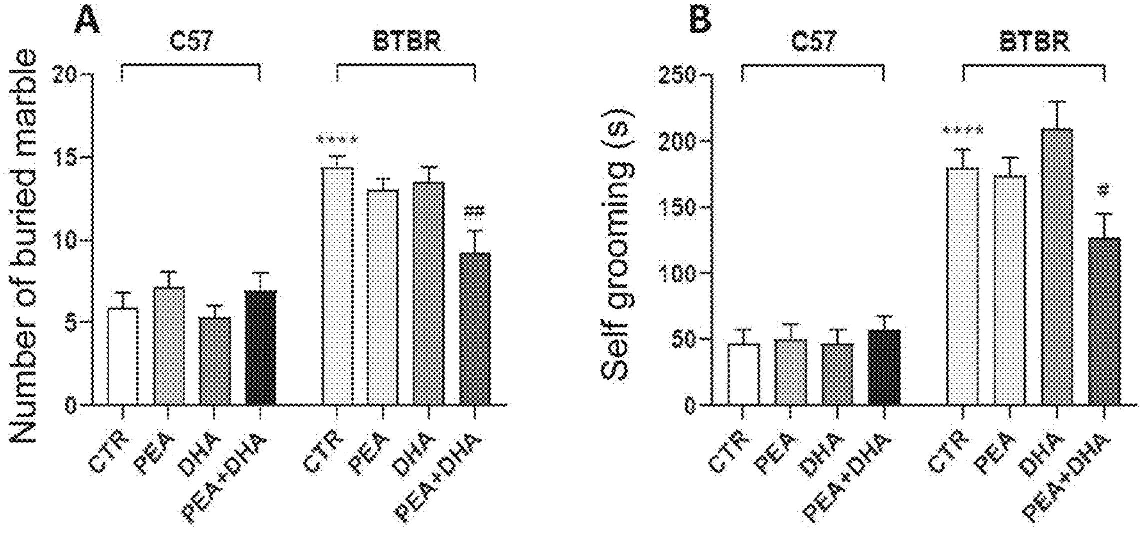
FIG. 2 shows the effect of the synergy of PEA-um associated with DHA on repetitive/obsessive behavior of BTBR mice. (A) Number of marbles buried in 15 min; (B) time spent self-cleaning by C57 and BTBR mice. All values are reported as mean±SEM of 8 animals for each group. ****$p<0.0001$ vs. C57 CTR; #$p<0.05$ vs. BTBR CTR; ##$p<0.01$ vs. BTBR CTR.

In the Marble Burying test, 20 marbles were placed in a grid inside a plexiglass cage filled with 5 cm of clean litter. Each mouse was placed in the cage and, after 15 session minutes, gently removed to count the number of buried marbles. The BTBR mice treated with only vehicle (CTR), only PEA-um 1 mg/kg (PEA) and only DHA 30 mg/kg (DHA), obsessively bury the marbles. Conversely, the treatment with PEA-um 1 mg/kg administered in combination with DHA 30 mg/kg significantly reduces the obsessive attitude of mice in hiding the marbles. As proof of the above, all the C57 animals (healthy animals) subjected to the treatments did not show significant changes in the number of buried marbles (FIG. 2A).

In the Self Grooming test, the mice were placed in an empty plexiglass cage (30×40 cm) and allowed to freely explore the arena. After 10 minutes of acclimatization, self grooming activity was monitored for 20 minutes. The repetitive attitude in washing the head, body, genital area and tail and in licking the arms and legs were taken into account.

Only treatment with PEA+DHA administered in combination is capable of reducing the seconds spent self-grooming by BTBR mice. The animals with ASD of the CTR, PEA and DHA groups did not demonstrate any reduction in the time (s) spent self-grooming (FIG. 2B). Again, in the C57 mice (healthy animals), no differences are observed between controls and treated animals.

Sociability of the Animals

Social interaction was examined using a three-chamber instrument. This test consists of 3 phases: in the first phase the animal is acclimatized for 5 minutes in the empty arena (center). In the next 10-minute session, the animal is exposed to an empty chamber on the left side of the instrument or to an unknown mouse in the right chamber.

In the last 10-minute phase, the preference of the mouse in staying in the empty chamber or in the presence of the mouse was evaluated (Crawley J N, *Designing mouse behavioral tasks relevant to autistic-like behaviors*, Ment. Retard Dev. Disabil. Res. Rev. 2004, 10: 248-258). The time spent in each chamber was detected by a camera coupled to video tracking software.

Figure 3:
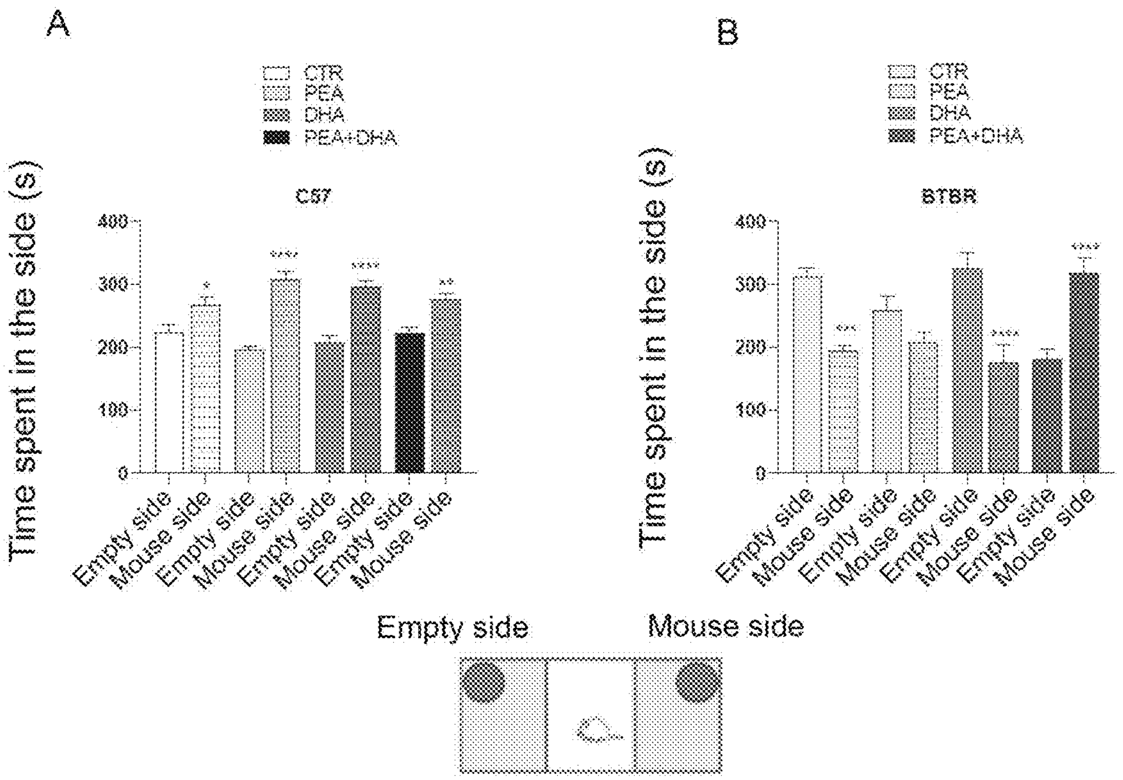
FIG. 3 shows the effect of all the treatments on the sociability of mice. (A) Time spent by C57 mice in the empty room or room occupied by a mouse; (B) same assessment for BTBR mice: only treatment with PEA+DHA is capable of improving the sociability of mice. All values are reported as mean±SEM of 8 animals for each group. *$p<0.05$ vs. C57 CTR; $p<0.01$ vs. C57 CTR; *$p<0.001$ vs. C57 CTR; ****$p<0.0001$ vs. C57 CTR.

The healthy C57 mice exhibit enhanced sociability to another mouse also following treatments with either only PEA-um or only DHA at the inactive concentrations of 1 mg/kg and 30 mg/kg (FIG. 3A). Conversely, in the BTBR mice, the sociability of which is reduced, only the synergy between PEA-um associated with DHA improves the sociability of autistic animals, leading the mice to spend more time in the company of a companion. The BTBR animals treated with vehicle, only PEA-um 1 mg/kg and only DHA 30 mg/kg did not demonstrate social improvements, continuing to spend their time in the empty side of the instrument (FIG. 3B).

Figure 4:
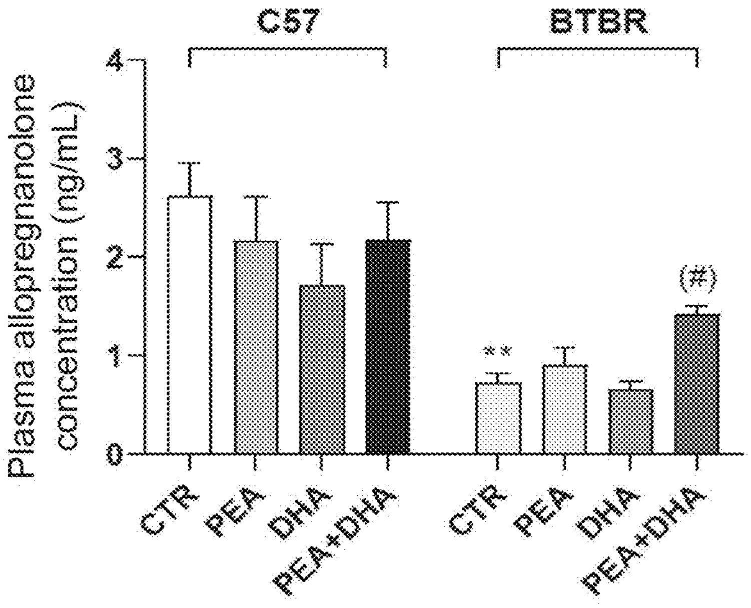
FIG. 4 shows the neurosteroidogenic effect of the synergy between PEA-um and DHA. PEA-um associated with DHA increases plasma ALLO levels of BTBR mice. PEA+DHA does not increase the plasma ALLO levels in C57 mice. All values are reported as mean±SEM of 8 animals for each group. **$p<0.01$ vs. C57 CTR; $^{(\#)}p<0.05$ vs. BTBR CTR.

Synergy Between PEA-Um Associated with DHA Increases Endogenous ALLO Neurosteroid Levels in ASD Mice BTBR mice have a significant reduction in plasma ALLO levels; this trend is also found in BTBR animals treated with PEA-um 1 mg/kg and DHA 30 mg/kg. Only the group of BTBR animals treated with the PEA-um 1 mg/kg+DHA 30 mg/kg combination has a significant increase in plasma levels of the neurosteroid ALLO. All the treatments performed in the healthy C57 mice did not induce any plasma ALLO increase (FIG. 4).

From the above demonstration, the synergistic effect resulting from the association between PEA and DHA allows to use lower dosages of both active substances than those normally used when such active ingredients are administered alone or, in the case of DHA, with other PUFAs, such as EPA.

The present invention thus provides a method for treating autism spectrum disorders (ASD) comprising or consisting in administering, to a subject suffering from ASD, PEA, preferably PEA in an ultra-micronized form, and DHA, where said administration is separate, combined (i.e., in a single dosage form) or simultaneous and where PEA and DHA are administered at a dosage at which, when administered alone, PEA and DHA are inactive.

Preferably, the doses of PEA-um and DHA administered to a child or adolescent patient are 500 mg/day or less and 700 mg/day, or more preferably 300 mg/day or less and 500 mg/day or less, respectively.

Furthermore, the present invention provides a method for increasing endogenous allopregnanolone levels in a subject in which said endogenous levels are below normal levels (i.e., preferably below 0.7 nmol/L), comprising or consisting in administering to said subject PEA, preferably in an ultra-micronized form, and DHA, where said administration is separate, combined (i.e., in a single dosage form) or simultaneous and where PEA and DHA are administered at a dosage at which, when administered alone, PEA and DHA are inactive.

Therefore, such a method allows the treatment not only of subjects with ASD, but also of subjects with depressive syndromes, in particular postpartum depression.

The invention will now be further described by means of the following formulation examples.

FORMULATION EXAMPLES

PEA-um=Ultra-micronized palmitoylethanolamide

Example 1—Soft Gelatin Capsules

12-Twist-Off Capsule Content:
- PEA-um 150.00 mg
- DHA (titer 55%) 435.00 mg
- Peanut oil 40.00 mg
- Soy lecithin 20.00 mg
- Alpha-tocopherol 10.00 mg
- Glyceryl monostearate 10.00 mg Composition of the Capsule:
- Bovine gelatin 237.00 mg
- glycerol 130.00 mg
- Water 19.00 mg
- Pigments 0.07 mg Example 2—Syrup Composition Per 100 ml:
- Sucrose 25.0 g
- Palmitoylethanolamide-m g 12.0
- DHA with 55% titer 5.0 g
- Microcrystalline cellulose 1.35 g
- Natural tocopherol (1000 IU/g) 1.0 g
- Sodium Carboxymethyl cellulose 0.65 g
- Sorbitan monooleate 0.40 g
- Polysorbate 80 0.10 g
- Natural flavoring 0.10 g
- Potassium sorbate 0.09 g
- Benzoic acid 0.07 g
- Citric acid 0.05 g
- Water q.s. to 100 ml Example 3—Dispersible Granules Contents of the Single-Dose Sachet:
- Palmitoylethanolamide 250 mg
- DHA powder with 17% titer 1400 mg
- Maltodextrin 500 mg
- Fructose 300 mg
- Dextrose 200 mg
- Tocopherol acetate 50% 200 mg (powder on silica)
- Citric acid 50 mg
- Pluronic F-68 50 mg
- Natural flavoring 50 mg
- Magnesium Stearate 10 mg
- Polysorbate 80 10 mg

We claim:

1. A method for the treatment of autism spectrum disorders (ASDs), wherein palmitoylethanolamide (PEA) in an ultra-micronized form is administered to a patient in association with docosahexaenoic acid (DHA), providing a synergistic effect, wherein said administration is separate, combined, or simultaneous and wherein, when said administration is combined, said palmitoylethanolamide and said DHA are present as a mixture, wherein a daily dosage of PEA and DHA for a child or adolescent subject are equal to or less than 500 mg/day and 700 mg/day respectively.

2. The method according to claim 1, wherein palmitoylethanolamide is in a non-micronized form, having a particle size distribution, defined as percentage by volume and measured by laser light scattering method, represented by a distribution curve having the mode above 10 microns.

3. The method according to claim 1, wherein palmitoylethanolamide is in a micronized form, having a particle size distribution, defined as percentage by volume and measured by laser light scattering method, represented by a distribution curve having the mode between 6 microns and 10 microns.

4. The method according to claim 1, wherein palmitoylethanolamide is in an ultra-micronized form having a particle size distribution, defined as percentage by volume and measured by laser light scattering method, represented by a distribution curve having the mode below 6 microns and above 0.5 microns.

5. The method according to claim 4, wherein palmitoylethanolamide has a particle size distribution, defined as percentage by volume and measured by the laser light scattering method, wherein at least 95% by volume, of particles has a particle size less than 6 microns.

6. The method according to claim 4, wherein palmitoylethanolamide has a particle size distribution, defined as a percentage by volume and measured by the laser light scattering method, having a mode between 2 and 4 microns and having 100% by volume of particles less than 10 microns and at least 60% by volume of particles less than 3 microns.

7. The method according to claim 1, wherein PEA and DHA are administered in a weight ratio between 1:7 and 7:1.

8. The method according to claim 4, wherein the PEA/DHA weight ratio is between 1:7 and 1:1.

9. The method according to claim 1, wherein palmitoylethanolamide and DHA are contained in pharmaceutical or veterinary formulations and are formulated in dosage forms for oral, buccal, parenteral, rectal, or transdermal administration.

10. The method according to claim 1, wherein palmitoylethanolamide and DHA are contained in dietary compositions, food supplements, or foods for special medical purposes (FSMPs).

11. The method according to claim 1, wherein the daily dosage of ultra-micronized PEA is 100 mg to 300 mg and the daily dosage of DHA is 200 mg to 500 mg.

12. The method according to claim 11, wherein the daily dosage of ultra-micronized PEA is 100 mg to 200 mg and the daily dosage of DHA is 200 mg to 300 mg.

13. A method for the treatment of subjects having endogenous levels of allopregnanolone which are lower than 0.7 nmol/L, which comprises or consists in administering PEA, and DHA to said subjects, wherein said administration is separate, combined, or simultaneous.

14. The method according to claim 13, for the treatment of depressive syndromes.

15. A composition comprising or consisting of a mixture of palmitoylethanolamide, and docosahexaenoic acid and pharmaceutically acceptable excipients, wherein palmitoylethanolamide and docosahexaenoic acid are contained in a weight ratio between 1:7 and 7:1 or, when palmitoylethanolamide is in an ultra-micronized form, in a weight ratio between 1:7 and 1:1.

16. A pharmaceutical or veterinary formulation, dietary compositions, food supplements, or foods for special medical purposes comprising the composition according to claim 15.

17. A composition for the treatment of autism spectrum disorders comprising:

ultra-micronized palmitoylethanolamide having a particle size distribution, defined as percentage by volume and measured by laser light scattering method, represented by a distribution curve having the mode below 6 microns and above 0.5 microns, wherein at least 95% by volume of particles has a particle size less than 6 microns, and a daily dosage of 100 mg to 300 mg per unit; and docosahexaenoic acid in an amount of 200 mg to 500 mg per unit dosage form.

* * * * *